United States Patent [19]

Kurita et al.

[11] 4,128,546

[45] Dec. 5, 1978

[54] PROCESS FOR THE PURIFICATION OF FR-1923 SUBSTANCE

[75] Inventors: Masaru Kurita, Takatsuki; Kazuyoshi Jomon, Kawanishi; Tadaaki Komori, Takatsuki; Isami Nakatani, Hata; Masahiro Tsuji, Osaka, all of Japan

[73] Assignee: Fujisawa Pharmaceutical Co., Ltd., Osaka, Japan

[21] Appl. No.: 694,906

[22] Filed: Jun. 10, 1976

Related U.S. Application Data

[63] Continuation-in-part of Ser. No. 562,928, Mar. 28, 1975, abandoned.

[51] Int. Cl.$^2$ ............................................. C07D 205/08
[52] U.S. Cl. ................................. 260/239 A; 424/118

[58] Field of Search ..................... 424/123; 260/239 A

[56] References Cited

U.S. PATENT DOCUMENTS

| | | | |
|---|---|---|---|
| 3,725,400 | 4/1973 | Voser | 260/243 C |
| 3,901,880 | 8/1975 | Scannell | 260/239 A |
| 3,923,977 | 12/1975 | Aoki et al. | 424/118 |

Primary Examiner—Donald G. Daus
Assistant Examiner—Mark L. Berch
Attorney, Agent, or Firm—Dayton R. Stemple, Jr.

[57] ABSTRACT

Purification of Fr-1923 antibiotic substance by treatment with a macroporous non-ionic adsorption resin such as styrene-divinyl benzene copolymer or acrylic ester polymer.

7 Claims, No Drawings

PROCESS FOR THE PURIFICATION OF FR-1923 SUBSTANCE

CROSS-REFERENCE TO RELATED APPLICATION

The present invention is a continuation-in-part application of copending application Ser. No. 562,928, filed Mar. 28, 1975, now abandoned.

DETAILED DESCRIPTION

The present invention relates to a new process for purification of FR-1923 substance. More particularly, it relates to a new process for purification of FR-1923 substance, using a macroporous non-ionic adsorption resin.

FR-1923 substance is a known antibiotic isolated from the fermentation broth of a strain of genus Nocardia as described, for example, in German Offenlegungsschrift No. 2,242,699 and U.S. Pat. No. 3923977 issued on Dec. 2, 1975, structure unknown. The structure is now believed to be

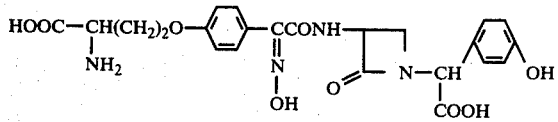

The said prior literatures disclose processes for isolation and purification of FR-1923 substance from a fermentation broth, using activated charcoal, anion exchange resin and DEAE-Sephadex (trademark, made by Pharmacia Co.). Cephaloxporin C, an antibiotic of different structure, has been purified with macroporous, nonionic resins as disclosed in U.S. Pat. No. 3,725,400.

However, the prior processes have not given satisfactory results in a scale of industrial manufacture of FR-1923 substance, because they require relatively many steps for the isolation and purification of FR-1923 substance, with a result the overall recovery of the antibiotic is relatively poor.

As the results of the extensive studying, the present inventors have now newly found a new process for purification of FR-1923 substance as a step in the recovery thereof, by means of which FR-1923 substance can be obtained in higher yield than by the prior processes. Further, this new process is simpler and more convenient in practical operation and more economical in an industrial scale, because the worn-out resin for purification can be regenerated for the repeated usage.

Accordingly, it is an object of the present invention to provide a new process for purification of FR-1923 substance, using a macroporous non-ionic adsorption resin.

Another object of the present invention is to provide a new process for purification of FR-1923 substance, by means of which FR-1923 substance is obtained in higher yield than by the prior processes.

A further object of the present invention is to provide a simpler, more convenient and more economical process for purification of FR-1923 substance.

As described above, the present invention provides a new process for purification of FR-1923 substance, using a macroporous non-ionic adsorption resin, which comprises alternative methods in a mode of using a macroporous non-ionic adsorption resin. In either embodiment of the present invention, an aqueous solution containing FR-1923 substance together with impurities is contacted with a macroporous non-ionic adsorption resin to adsorb FR-1923 substance to the resin. Thereafter, in method A the adsorbed FR-1923 substance is eluted with an eluent, for example, a hydrophilic solvent or an aqueous alkaline solution. In method B, further aqueous solution containing FR-1923 substance together with impurities is contacted with the macroporous non-ionic adsorption resin already saturated with FR-1923 substance to adsorb the impurities, and FR-1923 substance is recovered from the passed through solution.

Macroporous nonionic adsorption resins to be used in the methods of the present invention may have an average pore diameter of 4 to 100 nm and a surface from 100 to 1000 m² per gram.

Preferred examples of such resins may include a macroporous non-ionic styrene-divinyl benzene copolymer resin with an average pore diameter of 4 to 100 nm and a surface from 300 to 1000 m² per gram such as Amberlite XAD-1, XAD-2 and XAD-4 (trade mark, maker: Rohm & Haas Co.), Diaion HP 10, HP 20, HP 30, HP 40 and HP 50 (trade mark, maker: Mitsubishi Kasei Co., Ltd.) and a macroporous non-ionic acrylic ester polymer resin with an average pore diameter of 9 to 24 nm and a surface from 100 to 450 m² per gram such as Amberlite XAD-7 and XAD-8 (trade mark, maker: Rohm & Haas Co.).

These alternative methods are explained in more detail hereinafter.

METHOD A

According to method A of the present invention, there is provided a process for purification of FR-1923 substance, wherein an aqueous solution containing FR-1923 substance together with impurities is contacted with the macroporous non-ionic adsorption resin which is explained hereinabove, whereafter the adsorbed FR-1923 substance is eluted with an eluent, for example, a hydrophilic solvent or an alkaline aqueous solution.

The process for purification of FR-1923 substance, using the macroporous non-ionic adsorption resin, in accordance with the method A of the present invention is applicable to any aqueous solution containing FR-1923 substance together with impurities. As examples of such solutions to be treated for purification, there may be exemplified a filtrate of culture broth per se prepared by cultivating FR-1923 substance — producing microorganism in a nutrient medium and a pre-extracted culture solution as well as an aqueous solution comprising crude solid materials containing FR-1923 substance (e.g. crude powder or crude crystals containing FR-1923 substance) which are first isolated and purified to a certain extent from a filtrate of the culture broth in a conventional manner, such as an optional treatment of the filtrate with an appropriate solvent for extraction and/or by adsorption on activated charcoal.

Treatment of the aqueous solution containing FR-1923 substance together with impurities with the non-ionic adsorption resin according to this method is advantageously carried out under an acidic to neutral condition, that is at pH value of from 2-7 and preferably of from 4 to 6. The desired acidic pH values can be achieved by using any desired acid, for example, an organic acid such as oxalic acid or preferably a mineral acid such as hydrochloric, phosphoric or sulphuric acid.

In this method, the aqueous solution containing FR-1923 substance together with impurities is brought into contact with the macroporous non-ionic adsorption resin to adsorb FR-1923 substance in batch or column operation, and then the adsorbed FR-1923 substance is eluted from the resin in which FR-1923 is adsorbed with, for example, a hydrophilic solvent system.

The hydrophilic solvent system used for eluting FR-1923 substance from the resin, include, for example, a lower dialkyl ketone (e.g. acetone, methyl ethyl ketone, etc.), and a lower alkanol (e.g. methanol, ethanol, n-propanol, isopropanol, n-butanol, isobutanol, etc.) and the like. There may also be used mixtures of the above lower dialkylketone and lower alkanol. Further there may be also used, a mixtures of water or of a lower alkyl ester of a lower alkanoic acid (e.g. methyl acetate, ethyl acetate, butyl acetate, etc.) and the above lower alkanol or lower dialkyl ketone. Furthermore, a large volume of water and an alkaline aqueous solution (preferably pH 8 – 13) may be used, too.

The eluate thus obtained is treated by conventional means such as concentration, pH adjustment, lyophilization and recrystallization to give crystalline FR-1923 substance which frequently is sufficiently pure for a medical use.

With regard to this method A, it is to be noted that a filtrate of culture broth, and a pre-extracted culture solution as well as an aqueous solution comprising crude solid materials containing FR-1923 substance are optionally treated as mentioned above, and according to this method, especially a culture broth is effectively treated for purification to provide FR-1923 substance. Further, it is to be noted that this method is advantageously conducted especially when the impurities contained in the filtrate of culture broth, etc. are an inorganic salt such as sodium chloride, sodium biphosphate or disodium orthophosphate and the like.

METHOD B

According to method B of the present invention, there is provided a process for purification of FR-1923 substance wherein an aqueous solution containing FR-1923 substance together with impurities is contacted with the macroporous non-ionic adsorption resin already saturated with FR-1923 substance to adsorb impurities, and FR-1923 substance is recovered from the passed through solution. The macroporous non-ionic adsorption resin to be used is explained hereinabove.

This method is based on the fact that adsorption capacity of the macroporous non-ionic adsorption resin for FR-1923 substance is smaller than that for specific impurities such as coloring materials stemming from fermentation broth and isomer of FR-1923 substance which is produced in a fermentation broth as a by-product. By using the difference of affinity of the macroporous non-ionic adsorption resin for FR-1923 substance and for the specific impurities, the specific impurities are selectively adsorbed onto the resin already saturated with FR-1923 substance from an aqueous solution containing FR-1923 substance together with impurities, while FR-1923 substance passes through the resin to give a solution containing purified FR-1923 substance (i.e. passed through solution), from which FR-1923 substance is recovered by a conventional method.

Adsorption capacity of a macroporous non-ionic adsorption resin for FR-1923 substance varies with nature of aqueous solution containing FR-1923 substance and of impurities, and with nature of the macroporous non-ionic adsorption resin to be used. Examples of adsorption capacity of a macroporous non-ionic adsorption resin for FR-1923 substance are as follows. The following data is given by contacting 0.2M phosphate buffer solution (pH4) containing FR-1923 substance with the resin.

Examples of adsorption capacity to FR-1923 substance

Ca. 10g/l of Diaion HP 20
Ca. 18g/l of Amberlite XAD-4

The macroporous non-ionic adsorption resin saturated with FR-1923 substance is prepared by contacting an aqueous solution containing FR-1923 substance with the macroporous non-ionic adsorption resin, wherein pH range of said solution is 4 to 8, preferably 6 to 7.5.

The process for purification of FR-1923 substance, using the macroporous non-ionic adsorption resin according to this method B is applicable to any aqueous solution containing FR-1923 substance together with impurities, including those as mentioned above in connection with method A. Especially, when coloring materials or isomer of FR-1923 substance are contained as impurities in the aqueous solution, this method B gives better results.

When an aqueous solution containing FR-1923 substance together with impurities is contacted with the macroporous non-ionic adsorption resin already saturated by FR-1923 substance, FR-1923 substance can no longer be adsorbed onto the resin and passes through the resin, while the impurities are selectively adsorbed to the resin.

Volume of the macroporous non-ionic adsorption resin to be used in this method varies with a content of FR-1923 substance in an aqueous solution containing FR-1923 substance together with impurities and with nature of the resin to be used. Generally, the resin may be used in an amount of 1 per 100 – 500 g of FR-1923 substance in the aqueous solution.

Treatment of the aqueous solution containing FR-1923 substance together with impurities with the macroporous non-ionic adsorption resin saturated by FR-1923 substance is carried out at a pH value of 4 to 8, preferably of 6 to 7.5.

FR-1923 substance is recovered from the passed through solution containing purified FR-1923, which is obtained by contacting an aqueous solution containing FR-1923 substance together with impurities with macroporous non-ionic adsorption resin saturated by FR-1923 substance, in which FR-1923 substance passed through the resin to give an aqueous solution containing purified FR-1923 substance. The recovery can be conducted in conventional manners such as pH adjustment, treatment with activated charcoal, concentration, lyophilization and recrystallization to give crystalling FR-1923 substance which frequently is sufficiently pure for a medical use.

The worn-out resin can be regenerated in conventional manners, for examples, by washing the said resin with a relatively strong alkaline aqueous or alkaline aqueous-alcoholic solution.

The method B is superior to the method A and is more convenient in practice and more economical in an industrial scale, for the following reasons: That is, the method B does not require a process for elution of FR-1923 substance from the resin, and volume of the resin used for purification in method B is less than 10% of that used in method A, though the recovery and purity of FR-1923 substance are almost the same in both method. And, this method B is preferably used especially for purification of FR-1923 substance from pre-extracted culture solution or an aqueous solution comprising crude solid materials containing FR-1923 substance.

The following tests are given for the purpose of illustrating a comparison between method A and B as a process for purification of FR-1923 substance.

The comparison-tests are carried out by using the same crude crystals of FR-1923 substance and the same resin and the same volume of the resin in both methods; the volume of the crude crystals of FR-1923 substance in the method A is decided within the capacity of the resin for FR-1923 substance, and volume of the crude crystals of FR-1923 substance used in the method B is about 20 times that in method A.

TEST

[I] Adsorption capacity of Diaion HP 20 for FR-1923 substance:

1.4 g of sodium salt of FR-1923 (purity: 95%) substance were dissolved in 1 liter of 0.2 M phosphate buffer solution (pH 4.0). The solution was adjusted to pH 4.0 with 5N hydrochloric acid with stirring. The solution (concentration of FR-1923 substance: 1310 r/ml) was passed through a column packed with 100 ml of Diaion HP 20 (internal diameter of the column: 30 mm, packing height of the resin: 160 mm) at a rate of SV=1 ("SV" means abbreviation of "Space Velocity"). The passed through solution was collected 100ml by 100ml. The content of FR-1923 substance in the passed through solution was determined by bioassay using *Pseudomonas aeruginosa*. The adsorption capacity of Diaion HP 20 for FR-1923 substance was calculated at the time when concentration of FR-1923 substance in the passed through solution reaches the same concentration as that of the starting solution (1310 r/ml) to give 10.4 g/liter.

[II] Purification of FR-1923 substance by the method A:

9.5 g of crude crystals of FR-1923 substance (FR-1923 substance content: 7.9 g) were suspended in 2.5 liters of water. The suspension was adjusted to pH 7.5 with 6N aqueous sodium hydroxide solution to dissolve it. Further, the solution was adjusted to pH 6.0 with 6N hydrochloric acid, and to the solution there were added 150 g of sodium chloride and water to give 3 liters of the solution. The solution was passed through a column packed with 1 liter of Diaion HP 20 (internal diameter of the column: 77 mm, packing height of the resin: 230 mm) at a rate of SV=1. The adsorbed FR-1923 substance was eluted with 30% aqueous methanol after the column was washed with water. Active fraction (1950 ml) were collected and concentrated under reduced pressure. The concentrate was adjusted to pH 2.2 with stirring and allowed to stand overnight in the refrigerator to give crystals. The crystals were collected by filtration and dried. The results are shown in the following table.

[III] Purification of FR-1923 substance by the method B:

Two hundred gram of crude crystals of FR-1923 substance (FR-1923 substance content: 168 g) being the same crude crystals as used in Test [III], were suspended in 2 liters of water. The suspension was adjusted to pH 7.2 to dissolve it. The solution was passed through a column packed with 1 liter of Diaion HP 20 saturated by FR-1923 substance (internal diameter of the column: 77 mm, packing height of the resin: 230 mm) at a rate of SV=1. Four liters of water were passed through the column. 4500 ml of active fractions were collected from the passed through solution, and water was added to the solution to give 16 liters of the solution. The solution was adjusted to pH 2.5 with stirring and then allowed to stand overnight in the refrigerator to give crystals. The crystals were collected by filtration and dried. The results are shown in the following table.

|  | The method A | The method B |
| --- | --- | --- |
| Capacity of the resin for treating crude crystals of FR-1923 substance | 9.5 g/1l of resin | 187 g/1l of resin |
| Recovery of crystals | 7.2 g | 160 g |
| Purity of crystals | 92.7% | 98.4% |
| Purity-calcd.-recovery of FR-1923 substance | 84.5% | 93.6% |

The above results show that amount of FR-1923 substance treated by method B is about 20 times larger than that by method A, though the purity and recovery of FR-1923 substance are almost the same in both methods, respectively.

The following examples are given for the purpose of illustrating the present invention.

EXAMPLE 1

To a culture broth (pH 4.0) prepared by culturing *Nocardia uniformis* var. tsuyamanensis ATCC 21806 at 30° C for 120 hours in 150 liters of a nutrient medium containing by weight 3% glycerol, 2% cottonseed meal, 2% dried yeast, 2.18% potassium dihydrogen phosphate, 1.43% disodium hydrogen phosphate dodecahydrate, 0.5% magnesium chloride heptahydrate, there was added 6% of Radiolite (trade mark, a filter aid material sold by Showa Kagaku Kogyo Co., Ltd.) and then the mixture was filtered. Three liters of the filtrate obtained (FR-1923 substance content: 3030 mg) were passed through a column packed with a macroporous non-ionic adsorption resin, Diaion HP 20 (internal diameter of the column: 8 cm, packing height of the resin: 26 cm) at a rate of SV−1. The column was washed with water, whereafter FR-1923 substance was eluted with 20% of aqueous methanol solution. Three liters of eluate obtained were concentrated under reduced pressure and then adjusted to pH 2.5. The solution was allowed to stand in refrigerator to give 2490 mg of colorless crystals of FR-1923 substance.

EXAMPLE 2

A culture broth which was prepared in substantially the same manner as described in Example 1 was adjusted to pH 4.0 with diluted sulfuric acid, whereafter the culture broth was filtered. To the filtrate obtained was added 6% of Radiolite, whereafter the mixture was filtered. Nine hundred ml of the filtrate obtained (FR-1923 substance content: 774 mg) were passed through a column packed with a macroporous non-ionic adsorption resin, Amberlite XAD-4 (internal diameter of the column: 3.6 cm, packing height of the resin: 30 cm) at a rate of SV=1. After the column was washed with water, FR-1923 substance was eluted with 20% aqueous acetone. Six hundred ml of eluate obtained were concentrated under reduced pressure, adjusted to pH 2.0 with diluted hydrochloric acid, and then allowed to stand in a refrigerator to give 365 mg of colorless crystals of FR-1923 substance.

EXAMPLE 3

Three hundred ml of a culture filtrate (pH 4.0), obtained in substantially the same manner as described in Example 1, were passed through a column of a macroporous non-ionic adsorption resin, Diaion HP 20 (internal diameter of the column: 30 mm, packing height of the resin: 160 mm) at a rate of SV=1. The column was washed with water, whereafter FR-1923 substance was eluted with aqueous sodium hydroxide solution (pH 12.0). Six hundred ml of active fraction obtained were collected and concentrated to 15 ml under reduced pressure. The concentrate was adjusted to pH 2.5 with 6N hydrochloric acid while stirring, whereafter the solution was allowed to stand for 24 hours in the refrigerator to give 360 mg of colorless crystals of FR-1923 substance.

EXAMPLE 4

Twenty g of crude powder (FR-1923 substance content: 10.2 g) of FR-1923 substance were suspended in 6.2 l of water. The suspension was adjusted to pH 8.1 with 6N aqueous sodium hydroxide solution to dessolve it and then adjusted to pH 4.0 with hydrochloric acid, whereafter 50 g of sodium chloride were added to the solution. The solution was passed through a column of a macroporous non-ionic adsorption resin, Diaion HP 20 (internal diameter of the column: 87 mm, packing height of the resin: 520 mm) at a rate of SV=1. The column was washed with water, whereafter FR-1923 substance was eluted with 30% aqueous methanol solution. Active fractions (4.48 liters) obtained were collected and then concentrated to the volume of 400 ml under reduced pressure. The concentrate was adjusted to pH 2.5 with 6N hydrochloric acid and then allowed to stand overnight in refrigerator to give 10.0 g of colorless crystals of FR-1923 substance.

EXAMPLE 5

Eighteen gram of crude powder (FR-1923 substance content: 10.2 g) of FR-1923 substance were suspended in 360 ml of water, whereafter the suspension was adjusted to pH 7.0 with 6N sodium hydroxide aqueous solution to dissolve it. The solution was passed through a column packed with a macroporous non-ionic adsorption resin, Amberlite XAD-8 (internal diameter of the column: 30 mm, packing height of the resin: 160 mm) saturated by FR-1923 substance at a rate of SV=1, whereafter 400 ml of water were passed through the column. 700 ml of active fractions were collected from the passed solution, and then the solution was concentrated under reduced pressure to a volume of 200 ml. The concentrate obtained was adjusted to pH 2.5 with 6N hydrochloric acid while stirring, and then allowed to stand in a refrigerator for 24 hours to give 10.13 g of colorless crystals of FR-1923 substance.

EXAMPLE 6

Eighteen gram of crude powder (FR-1923 substance content: 10.2 g) of FR-1923 substance were suspended in 360 ml of water and adjusted to pH 7.0 with 6N aqueous sodium hydroxide solution to dissolve it. The solution was passed through a column packed with a macroporous non-ionic adsorption resin, Amberlite XAD-4 (internal diameter of the column: 30 mm, packing height of the resin: 160 mm) saturated by FR-1923 substance at a rate of SV=1, whereafter 540 ml of water were passed through the column. 900 ml of active fractions were collected from the passed solution, and then the solution was concentrated under reduced pressure to a volume of 350 ml. The concentrate obtained was adjusted to pH 2.5 with 6N hydrochloric acid while stirring and then allowed to stand in a refrigerator for 24 hours to give 9.42 g of colorless crystals of FR-1923 substance.

EXAMPLE 7

Nineteen gram of crude power (FR-1923 substance content: 10.7 g) of FR-1923 substance were suspended in 380 ml of water and then the suspension was adjusted to pH 7.0 with 6N aqueous sodium hydroxide solution to dissolve it. The solution was passed through a column packed with macroporous non-ionic adsorption resin, Amberlite XAD-7 (internal diameter of the column: 30 mm, packing height of the resin: 160 mm) saturated by FR-1923 substance at a rate of SV−1, whereafter 400 ml of water were passed through the column. 700 ml of active fractions were collected from the passed solution, whereafter the solution obtained was adjusted to pH 2.5 with 6N hydrochloric acid while stirring and allowed to stand in a refrigerator to give 10.28 g of colorless crystals of FR-1923 substance.

EXAMPLE 8

19.75 g of crude powder of FR-1923 substance (FR-1923 substance content: 17.16 g) were suspended in 395 ml of water and the suspension was adjusted to pH 7.5 with 5N aqueous sodium hydroxide solution to dissolve it. The solution was passed through a column packed with a macroporous non-ionic adsorption resin Diaion HP 20 (internal diameter of the column: 30 mm, packing height of the resin: 160 mm) saturated by FR-1923 substance at a rate of SV=1, whereafter 400 ml of water were passed through the column. 600 ml of active fractions were collected from the passed solution, whereafter the solution obtained was adjusted to pH 2.5 with 6N hydrochloric acid while stirring and allowed to stand in a refrigerator to give 16.8 g of colorless crystals of FR-1923 substance.

EXAMPLE 9

Fifteen liters of a culture filtrate (pH 4.0) (FR-1923 substance content: 14.25 g), obtained in substantially the same manner as described in Example 1, were passed through a column packed with a macroporous non-ionic adsorption resin, Diaion HP20 (internal diameter of the coulum: 110 mm, packing height of the resin: 550 mm) at a rate of SV=1. The column was washed with 5 liters of water, whereafter FR-1923 substance was eluted with 30% aqueous methanol solution. 7,940 ml of active fractions obtained were collected and then adjusted to pH 3.3 with 6N hydrochloric acid. The solution was passed through a column of alumina (acidic, internal diameter of the column: 46 mm, packing height of alumina: 300 mm). The column was washed with 500 ml of water, whereafter FR-1923 substance was eluted with 0.3 M pottassium biphosphate aqueous solution. 1800 ml of active fractions were collected and then concentrated under reduced pressure to the volume of 800 ml. The concentrate was adjusted to pH 2.2 with 6N hydrochloric acid while stirring, whereafter the solution was allowed to stand overnight in a refrigerator to give 11.94 g of colorless crystals of FR-1923 substance.

EXAMPLE 10

Thirty liters of a culture filtrate (pH 4.0) (FR-1923 substance content: 32.4 g), obtained in substantially the same manner as described in Example 1, were passed through a column packed with a macroporous nonionic adsorption resin, Diaion HP20 (internal diameter of the column: 140 mm, packing height of the resin: 600 mm) at a rate of SV=1. The column was washed with 10 liters of water, whereafter FR-1923 substance was eluted with 0.01 N sodium hydroxide aqueous solution. 30.1 liters of active fractions were collected and then adjusted to pH 3.3 with 6 N hydrochloric acid. The solution was passed through a column of alumina (acidic, internal diameter of the column: 77 mm, packing height of alumina: 440 mm). The column was washed with 2 liters of water, whereafter FR-1923 substance was eluted with 0.3M potassium biphosphate aqueous solution. 12.3 liters of active fractions were collected and then concentrated under reduced pressure to the volume of 1,600 ml. The concentrate was adjusted to pH 2.2 with 6H hydrochloric acid while stirring, whereafter the solution was allowed to stand overnight in a refrigerator to give 25.95 g of colorless crystals of FR-1923 substance.

EXAMPLE 11

Sixty g of crude powder of FR-1923 substance (FR-1923 substance content: 44.52 g) were suspended in 800 ml of water and the suspension was adjusted to pH 7.0 with 5 N sodium hydroxide aqueous solution to dissolve it. Water was added to the solution to give a volume of 1 liter, to which 1 liter of 6% aqueous sodium chloride solution was added. The aqueous solution was passed through a column packed with a macroporous nonionic adsorption resin, Diaion HP 20 (internal diameter of the column: 30 mm, packing height of the resin: 350 mm) saturated by FR-1923 substance at the rate of SV=1, whereafter 6 liters of 3% aqueous sodium chloride solution were passed through the column. 6 liters of active fractions were collected from the passed solution, whereafter the solution obtained was adjusted to pH 2.2 with 6 N hydrochloric acid while stirring and allowed to stand in a refrigerator to give 40 g of colorless crystals of FR-1923 substance.

We claim:

1. A process for treating impure FR-1923 substance to remove undesired components which comprises the steps of contacting an aqueous solution thereof at a pH of 4 – 8 with a macroporous nonionic adsorption resin selected from styrene-divinylbenzene copolymer and acrylic ester polymer, said resin having an average pore diameter of 4 to 100 nm and a surface from 100 to 1000 $m^2$ per gram, until said resin is saturated by FR-1923 substance, and thereafter contacting further aqueous solution of FR-1923 substance containing impurities at a pH of about 4 – 8 with said saturated resin to adsorb at least some of said second impurities, and recovering said further FR-1923 substance from the passed through solution.

2. A process according to claim 1 wherein said aqueous solutions are filtrates of culture broth.

3. A process according to claim 1 wherein said aqueous solutions are pre-extracted culture solutions.

4. A process according to claim 1 wherein said aqueous solutions are made from crude solid material of FR-1923 substance.

5. A process according to claim 1 wherein said aqueous solutions contain coloring materials as said impurities.

6. A process according to claim 1 wherein said aqueous solution contains said FR-1923 substance and an isomer thereof.

7. A process according to claim 1 wherein said resin is acrylic ester polymer.

* * * * *

UNITED STATES PATENT OFFICE
CERTIFICATE OF CORRECTION

PATENT NO. : 4,128,546
DATED : December 5, 1978
INVENTOR(S) : Masaru Kurita, et al.

It is certified that error appears in the above-identified patent and that said Letters Patent are hereby corrected as shown below:

Col. 1, line 34, change "cephaloxporin" to --cephalosporin--.
Col. 5, line 65, change "[III] to --[II]--.
Col. 8, line 9, change "9.42" to --9.41--.

Col. 8, line 21, change "SV-1" to --SV=1--.
Col. 9, line 24, change "6H" to --6N--.

Signed and Sealed this

Tenth Day of April 1979

[SEAL]

Attest:

RUTH C. MASON
Attesting Officer

DONALD W. BANNER
Commissioner of Patents and Trademarks